United States Patent
Sato et al.

(10) Patent No.: US 6,319,871 B1
(45) Date of Patent: Nov. 20, 2001

(54) DIELECTRIC MATERIAL

(75) Inventors: Motohiko Sato, Inazawa; Hitoshi Yokoi; Kazushige Ohbayashi, both of Nagoya, all of (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/385,470

(22) Filed: Aug. 30, 1999

(30) Foreign Application Priority Data

Aug. 31, 1998 (JP) .................................................. 10-246072

(51) Int. Cl.$^7$ ..................... C04B 35/462; C04B 35/465; C04B 35/468
(52) U.S. Cl. ..................... 501/139; 501/136; 501/137; 501/138
(58) Field of Search .................. 501/136, 137, 501/138, 139; 333/219.1, 202

(56) References Cited

U.S. PATENT DOCUMENTS

| | | | | |
|---|---|---|---|---|
| 3,975,307 | * | 8/1976 | Matsuo et al. | 501/139 |
| 4,119,554 | * | 10/1978 | Fujiwara | 501/136 |
| 4,283,753 | * | 8/1981 | Burn | 501/139 |
| 4,330,631 | | 5/1982 | Kawashima et al. | 501/139 |
| 4,764,494 | * | 8/1988 | Sakabe et al. | 501/139 |
| 4,781,859 | * | 11/1988 | Noi | 501/139 |
| 4,834,052 | * | 5/1989 | Hori et al. | 501/139 |
| 5,089,933 | * | 2/1992 | Saito et al. | 501/139 |
| 5,103,369 | * | 4/1992 | Saito et al. | 501/139 |
| 5,130,281 | * | 7/1992 | Sano et al. | 501/139 |
| 5,136,270 | | 8/1992 | Hatanaka et al. . | |
| 5,219,812 | * | 6/1993 | Doi et al. | 501/139 |
| 5,268,342 | * | 12/1993 | Nishiyama et al. | 501/139 |
| 5,612,654 | | 3/1997 | Tsujiguchi et al. . | |
| 5,650,368 | * | 7/1997 | Tateishi et al. | 501/139 |
| 5,686,367 | * | 11/1997 | Hayashi | 501/139 |
| 5,801,111 | * | 9/1998 | Wada et al. | 501/139 |
| 5,827,792 | * | 10/1998 | Fukuda et al. | 501/139 |
| 5,977,006 | * | 11/1999 | Iguchi et al. | 501/139 |
| 6,051,516 | * | 4/2000 | Mizuno et al. | 501/139 |

FOREIGN PATENT DOCUMENTS

| | | | |
|---|---|---|---|
| 0 205 137 A | 12/1986 | (EP) . | |
| 0 873 979 A1 | 10/1998 | (EP) . | |
| 63-222064 | 9/1988 | (JP) | C04B/35/00 |
| 2736439 | 1/1998 | (JP) | C04B/35/46 |
| 2840673 | 10/1998 | (JP) | C04B/35/46 |
| 59-37526 | 9/1984 | (JP) | H01B/3/12 |
| 61-17083 | 5/1986 | (JP) | H01B/3/12 |
| 6-309926 | 11/1994 | (JP) | H01B/3/12 |
| 6-325620 | 11/1994 | (JP) | H01B/3/12 |

OTHER PUBLICATIONS

XP–002123199—Abstract 11/94.
XP–002123200—Abstract 11/94.
European Search Report 11/99.

* cited by examiner

*Primary Examiner*—Michael Marcheschi
(74) *Attorney, Agent, or Firm*—Sughrue, Mion, Zinn, Macpeak & Seas, PLLC

(57) ABSTRACT

Disclosed is a dielectric material comprising: a main ingredient having a composition represented by $xBaO-yRE_2O_3-zTiO_2$, wherein RE represents at least one rare earth element, and $x+y+z=100$ mol %; at least one alkali metal oxide; and an ingredient derived from an oxygen supplying agent which releases oxygen on heating.

7 Claims, 3 Drawing Sheets

DIELECTRIC MATERIAL

BACKGROUND OF THE INVENTION

1. Field of the Invention

This invention relates to a dielectric material. More particularly, it relates to a dielectric material which is obtained by sintering while suppressing reduction reaction in the inside thereof and therefore exhibits stable dielectric characteristics. The dielectric material of the present invention has excellent dielectric characteristics, i.e., a relatively high relative dielectric constant (hereinafter represented by $\in_r$), a small absolute value of the temperature coefficient of resonance frequency (hereinafter resonance frequency is represented by $f_o$, and the temperature coefficient thereof is represented by $\tau_f$), and a large value of unloaded quality coefficient (hereinafter represented by $Q_u$). The dielectric material of the present invention is suited for use in multi-layer circuit boards, resonators and filters particularly for use in a high frequency region, an impedance matching element for various microwave circuits, and the like.

2. Description of the Related Art

With the recent increase of communication information, rapid progress is being made in various communication systems utilizing the microwave region, such as mobile telecommunication systems, satellite communication systems, positioning systems using communication data, and satellite broadcasting. Many microwave dielectric materials have been developed accordingly. Microwave dielectric materials for these uses are required to have (1) a high relative dielectric constant $\in_r$, (2) a small absolute value of the temperature coefficient $\tau_f$ of resonance frequency $f_o$ (i.e., small temperature dependence of $f_o$), and (3) a large unloaded quality coefficient $Q_u$ (i.e., a small dielectric loss $1/Q_u$).

$Ba(Mg_{1/3}Ta_{2/3})O_3$ and $Ba(Zn_{1/3}Ta_{2/3})O_3$ are known to be dielectric materials having a small dielectric loss, i.e., a large $Q_u$. In Japanese Patent 2736439 is disclosed a dielectric porcelain composition based on $BaO-Nd_2O_3-Sm_2O_3-TiO_2-Bi_2O_3$ having incorporated therein an Mn oxide. Additionally, a dielectric porcelain composition containing an Mn compound and having a high dielectric constant is disclosed in JP-B-61-17083 and Japanese Patent 2840673.

However, depending on the components contained, cases sometimes occur with these known dielectric materials, in which the inside of the material (sintered body) is in a reduced state due to shortage of oxygen during sintering, failing to exhibit stable dielectric characteristics. This is particularly observed with large sintered bodies such as those used in large-sized resonators.

SUMMARY OF THE INVENTION

An object of the present invention is to provide a dielectric material which can be obtained by firing at a relatively low temperature and stably exhibits a high $\in_r$, a small absolute value of $\tau_f$, and a large $Q_u$ irrespective of the volume of the sintered body.

The entire disclosure of each and every foreign patent application from which the benefit of foreign priority has been claimed in the present application is incorporated herein by reference, as if fully set forth.

DETAILED DESCRIPTION OF THE INVENTION

Figure 1:
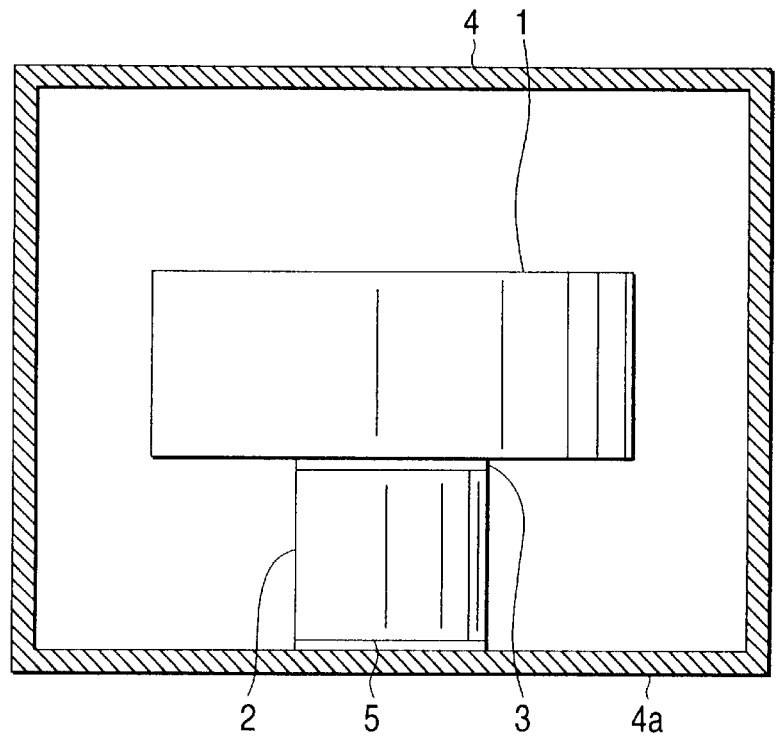
FIG. 1 illustrates a dielectric resonator utilizing the dielectric material of the present invention.

The dielectric material according to the present invention comprises a main ingredient having a composition represented by $xBaO-yRE_2O_3-zTiO_2$ (wherein RE represents at least one rare earth element, and $x+y+z=100$ mol %), at least one alkali metal oxide, and an ingredient derived from an oxygen supplying agent which releases oxygen on heating.

The main ingredient is preferably present in an amount of 90 parts by weight or more, particularly 95 parts by weight or more, per 100 parts by weight of the dielectric material.

The oxygen supplying agent is a compound capable of supplying oxygen to a green body to be sintered on firing. Since the oxygen supplying agent supplies sufficient oxygen to the inside of the green body, sintering can be achieved without adopting a special firing technique, such as oxygen-enriched firing. It is desirable for the oxygen supplying agent to thermally decompose on heating to release oxygen, to give little adverse influence to dielectric characteristics of the resultant sintered body, and to be capable of supplying much oxygen for its small amount. The heating temperature at which oxygen is to be released is about 800 to 1450° C., preferably about 900 to 1400° C. Where sintering is to be performed simultaneously with the heating for oxygen supply, that temperature can be set at about 1100 to 1450° C., preferably 1200 to 1400° C., still preferably 1250 to 1400° C.

It is also desirable that the oxygen supplying agent be a compound that easily releases oxygen atoms. From this viewpoint, the oxygen supplying agent is preferably a metal compound containing an oxygen atom and at least one metal atom having two or more stable oxidation numbers (inclusive of relatively stable or more stable oxidation numbers), and the oxidation number of the metal atom in the metal compound is not the smallest one. In other words, the metal atom in the metal compound is reduced in a sintered body and yet exists in the sintered body with a smaller oxidation number. Metal atoms that constitute such metal compounds include V, Cr, Mn, Fe, Co, Ni, Cu, Ga, Ge, Nb, Mo, Tc, Ru, Rh, Pd, Ag, In, Sn, Sb, Ta, W, Re, Os, Ir, Pt, Au, Tl, Pb, Bi, and Po. Among these metal atoms particularly preferred are Mn, Cu, Ag, Sn, Pb, and a combination thereof because the metal compounds containing them manifest their effects even in a trace amount.

The metal compounds containing the above-described metal atoms are preferably those containing as many oxygen atoms as possible per molecule and those metal oxides having a high equivalent ratio of oxygen atoms to the metal atoms per molecule so as to supply as much oxygen as possible to the green body.

Examples of such metal compounds include not only oxides but carbonates, nitrates and sulfates of the above-described metals, e.g., V, Cr, Mn, Fe, Co, Ni, Cu, Ga, Ge, Nb, Mo, Tc, Ru, Rh, Pd, Ag, In, Sn, Sb, Ta, W, Re, Os, Ir, Pt, Au, Tl, Pb, Bi, and Po. Permanganic acid, chromic acid and salts thereof are also useful. Preferred of them are $MnO_2$, $CuO$, $AgO$, $SnO_2$, $PbO_2$ and a combination thereof. $V_2O_5$, $Nb_2O_5$, $Cr_2O_3$, $WO_3$, and the like are also useful as a metal compound.

The oxygen supplying agent is preferably used in an amount of 0.01 to 5 parts by weight per 100 parts by weight of the main ingredient. If the amount is within this range, the effects of the present invention can be preferably attained without deteriorating the dielectric characteristics of the resulting sintered body.

While the oxygen supplying agent is effective in producing dielectric materials having a relatively small volume, e.g., about 3 cm$^3$, it is particularly effective when used in the production of dielectric materials having a relatively large volume, e.g., about 25 cm$^3$ or more, preferably about 40 cm$^3$ or more, and especially about 800 cm$^3$ or more, in attaining markedly improved dielectric characteristics as compared with the dielectric materials produced without the oxygen supplying agent.

In the main ingredient having a composition represented by $xBaO$—$yRE_2O_3$—$zTiO_2$, the molar ratio of BaO, represented by x, is preferably greater than 0 and not greater than 27.0, still preferably from 5.0 to 22.5. BaO, particularly being present in an amount of 5.0 mol % or higher, especially 10.0 mol % or more, brings about sufficient improvement in $\in_r$. If the molar ratio of BaO exceeds 27.0 mol %, $Q_u$ tends to decrease.

The molar ratio (y) of $RE_2O_3$ is preferably greater than 0 and not greater than 30.0 mol %, still preferably 21.0 mol % or less. $RE_2O_3$, particularly when present in an amount of 4.0 mol % or more, especially 11.0 mol % or more, sufficiently diminishes the absolute value of $\tau_f$. Existence of more than 30.0 mol % of $RE_2O_3$ is apt to reduce $Q_u$.

The rare earth element RE in $RE_2O_3$ is preferably at least one of La, Ce, Pr, Nd, and Sm. Still preferably, $RE_2O_3$ is a rare earth oxide represented by composition formula: $\{(1-a-b-c-d)Sm.aLa.bCe.cPr.dNd\}_2O_3$, wherein $0 \leq a<1$, $0 \leq b<1$, $0 \leq c<1$, $0 \leq d<1$, and $a+b+c+d<1$. In other words, the preferred $RE_2O_3$ comprises at least Sm and consists of samarium oxide alone or samarium oxide with part of Sm replaced with at least one of La, Ce, Pr, and Nd.

$RE_2O_3$ can be incorporated into the main ingredient by adding, to a mixture of powdered raw materials, the rare earth oxides or precursors thereof which produce the corresponding oxides on heating, such as oxalates, nitrates, sulfates or chlorides of the rare earth elements.

The molar ratio (z) of $TiO_2$ is preferably 55.0 or greater and smaller than 100.0, still preferably 62.5 or greater and less than 95.0. $TiO_2$, being present in an amount of 55.0 mol % or more, especially 62.5 mol % or more, improves $Q_u$ sufficiently. With the molar ratio of $TiO_2$ being less than 95.0 mol %, particularly less than 80.0 mol %, the absolute value of $\tau_f$ can be reduced further.

The alkali metal oxide which can be used in the present invention is preferably the oxide of at least one alkali metal selected from lithium, sodium, and potassium. These alkali metal oxides are easy to handle and inexpensive. The alkali metal oxide is effective in lowering the firing temperature for sintering, making it possible to produce a sufficiently dense sintered body at a reduced sintering temperature.

The content of the alkali metal oxide in the dielectric material of the present invention is preferably up to 5 parts by weight per 100 parts by weight of the main ingredient. If it exceeds 5 parts by weight, sintering does not proceed stably. It will follow that the resulting dielectric material has a reduced $Q_u$ and that the $\tau_f$ shifts to the minus side to have an increased absolute value. A preferred alkali metal oxide content is from 0.1 to 5 parts by weight. Even with the alkali metal oxide content being as small as 0.1 to 2.0 parts, particularly 0.2 to 1.0 part, a dielectric material having excellent dielectric characteristics can be obtained in a stable manner.

In producing the dielectric material, the alkali metal oxide can be added to a mixture of powdered raw materials either in the form of the alkali metal oxide itself or a corresponding alkali metal compound capable of producing the oxide on heating, such as the carbonate, oxalate, nitrate or sulfate of the alkali metal.

The present invention preferably provides a dielectric material having a value of $\in_r$ of 50 to 100, a product of $Q_u xf_0$ of 5,000 to 20,000 GHz, a value of $\tau_f$ of from −20 to +20 ppm/° C.

In producing a dielectric material of relatively large volume, there is the problem that the oxygen in the firing atmosphere and the oxygen present in the green body of starting materials are insufficient for supplying oxygen deep into the central portion of the green body, tending to fail to attain a satisfactory oxidized state. As a result, the resulting sintered body may have portions in a reduced state in the inside thereof. It is difficult to obtain stable dielectric characteristics from a sintered body having such a non-uniform oxidized state. In order to eliminate this disadvantage, it has been a practice commonly followed that sintering is carried out in an oxygen-enriched atmosphere or, in some cases, annealing is conducted. To the contrary, according to the present invention wherein the starting material contains an alkali metal oxide which, even in a slight amount, enables low-temperature sintering and an oxygen supplying agent, the oxygen-supplying agent decomposes even at a relatively low heating temperature to generate oxygen thereby supplying sufficient amount of oxygen to the green body.

The present invention will now be illustrated in greater detail by reference to Examples, but it should be understood that the invention is not construed as being limited thereto.

EXAMPLES 1 TO 15

Predetermined amounts of commercially available powders of $BaCO_3$, $Sm(OH)_3$, $TiO_2$, $A_2CO_3$ (wherein A represents an alkali metal), and an oxygen supplying agent shown in Table 1 below were weighed out to give the final composition shown in Table 1 in terms of the respective oxides. The compositions shown in Table 1 correspond to the main ingredients represented by $xBaO$—$yRE_2O_3$—$zTiO_2$ in which $RE_2O_3$ is $Sm_2O_3$ (i.e., a=b=c=d=0).

The powders were wet mixed using ethanol as a medium, and the mixed powder was calcined in the air atmosphere at 1000° C. for 2 hours. The calcined product was pulverized in a ball mill together with a wax binder, a dispersant, and ethanol. The resulting slurry was dried, granulated, and compacted under a pressure of 10 to 20 MPa into a cylindrical form of 20 mm in diameter and 12 mm in thickness. The cylindrical compact was subjected to cold isostatic pressing (CIP) under a pressure of 150 MPa, and then sintered by firing at 1350° C. for 2 hours in the air atmosphere to obtain a sintered body.

After surface grinding, the resulting sintered body, i.e., dielectric material, was examined for $\in_r$, $Q_u$, and $\tau_f$ by the Hakki and Coleman's method in a frequency range of from 2 to 4 GHz at a measuring temperature of from 25 to 80° C. The results obtained are shown in Table 1, in which all the parts are given by weight.

TABLE 1

| Sample No. | Main Ingredient BaO x | Main Ingredient $Sm_2O_3$ y | Main Ingredient $TiO_2$ z | Alkali Metal Oxide Kind of Metal | Alkali Metal Oxide Amount (parts) | Oxygen Supplying Agent Kind | Oxygen Supplying Agent Amount (parts) | Dielectric Characteristics $\epsilon_r$ | Dielectric Characteristics $Q_u \times f_0$ (GHz) | Dielectric Characteristics $\tau_\epsilon$ (ppm/° C.) | Remark |
|---|---|---|---|---|---|---|---|---|---|---|---|
| 1 | 17.5 | 5.0 | 77.5 | K | 0.25 | $MnO_2$ | 1.0 | 53 | 12000 | 2 | invention |
| 2 | 17.5 | 5.0 | 77.5 | K | 0.50 | $MnO_2$ | 3.0 | 54 | 13000 | 7 | " |
| 3 | 17.5 | 15.0 | 67.5 | Na | 0.25 | $SnO_2$ | 2.0 | 78 | 7700 | 6 | " |
| 4 | 12.5 | 10.0 | 77.5 | Na | 0.75 | $MnO_2$ | 0.3 | 70 | 7500 | −14 | " |
| 5 | 12.5 | 10.0 | 77.5 | Na | 1.00 | $MnO_2$ | 4.0 | 72 | 8000 | −10 | " |
| 6 | 15.0 | 15.0 | 70.0 | Li | 0.50 | $MnO_2$ | 1.5 | 85 | 7500 | 5 | " |
| 7 | 15.0 | 15.0 | 70.0 | Na | 1.00 | AgO | 3.0 | 78 | 8500 | 1 | " |
| 8 | 12.5 | 15.0 | 72.5 | K | 1.00 | $MnO_2$ | 0.1 | 73 | 9000 | −8 | " |
| 9 | 12.5 | 15.0 | 72.5 | K | 1.50 | $MnO_2$ | 0.5 | 71 | 9500 | 2 | " |
| 10 | 10.0 | 20.0 | 70.0 | Na | 0.50 | $MnO_2$ | 0.7 | 76 | 7500 | −8 | " |
| 11 | 10.0 | 10.0 | 80.0 | Na | 1.25 | $PbO_2$ | 1.0 | 88 | 6300 | −9 | " |
| 12 | 20.0 | 7.5 | 72.5 | Na | 0.50 | $MnO_2$ | 3.5 | 69 | 8700 | −11 | " |
| 13 | 20.0 | 7.5 | 72.5 | Na | 1.00 | $MnO_2$ | 5.0 | 62 | 9500 | −8 | " |
| 14 | 10.0 | 20.0 | 70.0 | Na | 0.50 | $MnO_2$ | 0.0 | 73 | 6500 | −15 | comparison |
| 15 | 10.0 | 7.5 | 82.5 | Na | 2.00 | $MnO_2$ | 6.0 | 75 | 2600 | 70 | " |

It is seen from Table 1 that the dielectric materials according to the present invention have the absolute value of $\tau_f$ controlled within a very narrow range (e.g., 14 or less) and a $Q_u x f_0$ value as high as 6,300 GHz or more. In particular, the $Q_u x f_0$ of sample No. 2 reached 13,000 GHz. Further, the $\epsilon_r$ of the dielectric materials of the invention can be selected from a broad range of from 53 to 88. Therefore, the present invention applies widely to small to large-volume dielectric materials.

More specifically, sample No. 1, whose $\epsilon_r$ is 53, is especially suited to production of relatively large-sized dielectric parts and yet exhibits extremely excellent dielectric characteristics as having $Q_u x f_0$ of 12,000 GHz and $\tau_f$ of 2 ppm/° C. On the other hand, sample Nos. 7 and 9 have a relatively large $\epsilon_r$ value compared with sample No. 1 while exhibiting well-balanced dielectric characteristics ($\epsilon_r$: 78 and 71, respectively; $Q_u x f_0$: 8,500 GHz and 9,500 GHz, respectively; and $\tau_f$: 1 ppm/° C. and 2 ppm/° C., respectively) and are therefore useful in production of relatively small-sized dielectric parts.

Furthermore, Sample Nos. 10' and 14' were prepared in the same manner as Sample Nos. 10 (including $MnO_2$) and 14 (including no $MnO_2$) except for changing the size of the cylindrical compact (20 mm in diameter and 12 mm in thickness) to 40 mm in diameter and 24 mm in thickness. The dielectric characteristics of Sample Nos. 10' and 14' were measured in the same manner as in Sample Nos. 10 and 14.

The results obtained are shown in Table 1' below.

TABLE 1'

| Sample No. | Dielectric characteristics |
|---|---|
| 10 | $\epsilon_r$ = 76, $Q_u \times f_o$ = 7, 500 GHz, $\tau_f$ = −8 ppm/° C. |
| 10' | $\epsilon_r$ = 76, $Q_u \times f_o$ = 7, 500 GHZ, $\tau_f$ = −8 ppm/° C. |
| 14 | $\epsilon_r$ = 73, $Q_u \times f_o$ = 6, 500 GHZ, $\tau_f$ = −15 ppm/° C. |
| 14' | Measurement is impossible due to dielectric characteristics deterioration |

As is clear from the results of Table 1', while Sample No. 14' deteriorated dielectric characteristics when the size was enlarged, Sample No. 10' including MnO2 maintained dielectric characteristics even if the size was enlarged.

EXAMPLES 16 TO 27

Dielectric materials were produced in the same manner as for sample No. 8, except for replacing part of the samarium oxide ($Sm_2O_3$) with other rare earth oxides as shown in Table 2 below. The resulting dielectric materials were evaluated in the same manner as in Examples 1 to 15. The results obtained are shown in Table 2.

TABLE 2

| Sample No. | Proportion of Rare Earth Oxides $Sm_2O_3$ | Proportion of Rare Earth Oxides $La_2O_3$ y | Proportion of Rare Earth Oxides $CeO_2$ | Proportion of Rare Earth Oxides $Pr_6O_{11}$ | Proportion of Rare Earth Oxides $Nd_2O_3$ | Dielectric Characteristics $\epsilon_\gamma$ | Dielectric Characteristics $Q_u \times f_0$ (GHz) | Dielectric Characteristics $\tau_\epsilon$ (ppm/° C.) |
|---|---|---|---|---|---|---|---|---|
| 8 | 15.0 | — | — | — | — | 73 | 9000 | −8 |
| 16 | 13.5 | 1.5 | — | — | — | 76 | 8600 | −2 |
| 17 | 12.0 | 3.0 | — | — | — | 80 | 8400 | 10 |
| 18 | 10.0 | 4.5 | — | — | — | 88 | 8100 | 27 |
| 19 | 14.3 | — | 0.7 | — | — | 75 | 8800 | −14 |
| 20 | 13.5 | — | 1.5 | — | — | 78 | 8700 | −11 |
| 21 | 12.8 | — | 2.2 | — | — | 81 | 8400 | −7 |
| 22 | 14.5 | — | — | 0.5 | — | 74 | 9000 | −5 |
| 23 | 14.1 | — | — | 0.9 | — | 76 | 8600 | 2 |
| 24 | 13.6 | — | — | 1.4 | — | 79 | 8600 | 6 |
| 25 | 11.2 | — | — | — | 3.8 | 75 | 9500 | −6 |

TABLE 2-continued

| Sample No. | Proportion of Rare Earth Oxides | | | | | Dielectric Characteristics | | |
|---|---|---|---|---|---|---|---|---|
| | $Sm_2O_3$ | $La_2O_3$ | $CeO_2$ y | $Pr_6O_{11}$ | $Nd_2O_3$ | $\epsilon_\gamma$ | $Qu \times f_0$ (GHz) | $\tau_\epsilon$ (ppm/° C.) |
| 26 | 7.5 | — | — | — | 7.5 | 77 | 9400 | −3 |
| 27 | 3.8 | — | — | — | 11.2 | 80 | 9000 | 3 |

It can be seen from the results in Table 2 that all the dielectric materials (sample Nos. 16 to 27) containing rare earth oxides represented by $RE_2O_3$ exhibit excellent dielectric characteristics and that the $\tau_f$ is shifted to the plus side, the $Q_u \times f_0$ decreases, and $\in_\gamma$ increases according as the proportion of the rare earth elements other than samarium increases. Thus these results prove that dielectric materials having well-balanced properties can be obtained by properly adjusting the ratio of samarium and other rare earth elements in $RE_2O_3$.

While the invention has been described in detail and with reference to specific examples thereof, various changes and modifications can be made therein without departing from the spirit and scope thereof. For example, the dielectric materials may contain other components in addition to the main ingredient and the alkali metal oxide or unavoidable impurities as long as the dielectric characteristics are not substantially affected thereby.

(1) An Example of Dielectric Resonator Prepared by Using Dielectric Material of the Invention The dielectric material of the present invention may be used in a dielectric resonator described in U.S. Pat. No. 5,136,270, hereby incorporated by reference.

FIG. 1 illustrates an example of such a dielectric resonator of providing resonator body 1 comprising the dielectric material of the present invention. The resonator body is bonded to one end of holding member 2 by means of, for example, an epoxy resin type adhesive 3. The integrated resonator body 1 and holding member 2 are contained in the inside of metal container 4 of a cylindrical shape the both end surface of which are sealed up. One end of the holding member 2 is fixed and bonded to the center of the bottom surface 4a of the metal container 4 by means of PTTF 5.

(2) An Example of Dielectric Filter Prepared by Using Dielectric Material of the Invention The dielectric material of the present invention may be used in a dielectric filter described in U.S. Pat. No. 5,537,085, hereby incorporated by reference.

Figure 2:
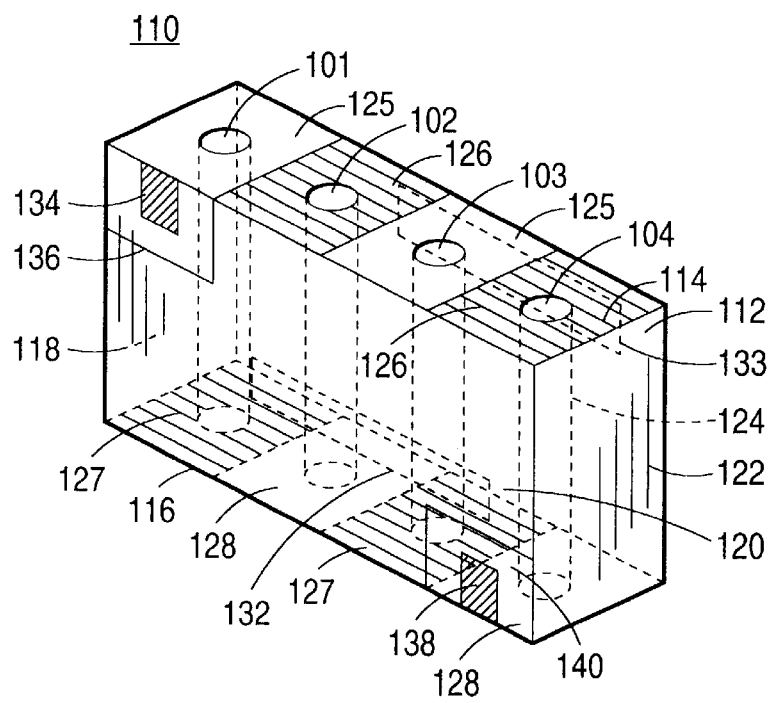
FIG. 2 illustrates a dielectric filter utilizing the dielectric material of the present invention.

FIG. 2 illustrates an example of such a four pole high zero interdigital block filter 110. The filter 110 includes a filter body 112 having a block of the dielectric material of the present invention and having top and bottom surfaces 114 and 116 and side surfaces 118, 120, 122 and 124. The filter body has a plurality of through-holes extending from the top surface to the bottom surface 114 to 116 defining a first resonator 101, a second resonator 102, a third resonator 103, and a fourth resonator 104.

The surfaces 118, 120, 122 and 124 are substantially covered with a conductive material defining a metallized exterior layer, with the exception that the top surface 114 and the bottom surface 116 are selectively metallized in the areas substantially surrounding the resonators defining an interdegital filter design. More specifically, top surface 114 adjacent to a first and a third resonator 101 and 103 are unmetallized 125, and a bottom surface 116 adjacent to a second 102 and a fourth resonator 104 are unmetallized 128. To complete the interdigital design, the bottom surface 116 adjacent to a first and a third resonator 101 and 103 are metallized 127, and the top surface adjacent to the second and a fourth resonator 104 are metallized 126.

Additionally, a portion of one of the side surfaces is substantially uncoated (comprising the dielectric material) in proximity to one of the ends of the block, and extends at least in proximity to between alternate resonators, defining a magnetic transmission line 132 for magnetically coupling the resonators. The ceramic filter 110 also includes first and second input-output means, and preferably in the form of pads 134 and 138 comprising an area of conductive material on at least one of the side surfaces and substantially surrounded by at least one or more uncoated areas 136 and 140 of the dielectric material.

In this embodiment, the input-output pads 134 and 138 are offset on opposite ends of the block. This is necessary because the input-output pads are located near the non-grounded ends of their respective resonators to achieve maximum electrical coupling. In the four-pole resonator design in FIG. 2, the first resonator 101 and the fourth resonator 104 are grounded at opposite ends of the block filter 110, thus requiring the input-output pads to be offset at opposite ends of the block.

The magnetic transmission line 132 may be located on the front surface of the block 120, on the rear surface of the block 124, or both the front and rear surfaces of the block as design parameters dictate. However, in a preferred embodiment, only a single magnetic transmission line 132 is placed on the rear surface 124 opposite to the surface 120 containing the input-output pads 134 and 138.

The magnetic transmission line 132 can be varied to achieve maximum design flexibility. In this embodiment, the magnetic transmission line 132 may extent laterally at least in proximity to the first and third resonators or it may extend laterally in proximity to the second and fourth resonators, shown as item 133 in FIG. 2. The four pole interdigital block filter 110 can lead to a product which is easier to manufacture, and require less processing steps, than conventional four pole ceramic block filters.

(3) A second Example of Dielectric Filter Prepared by Using Dielectric Material of the Invention The dielectric material of the present invention may be used in a dielectric filter described in U.S. Pat. No. 5,612,654, hereby incorporated by reference.

Figure 3A:
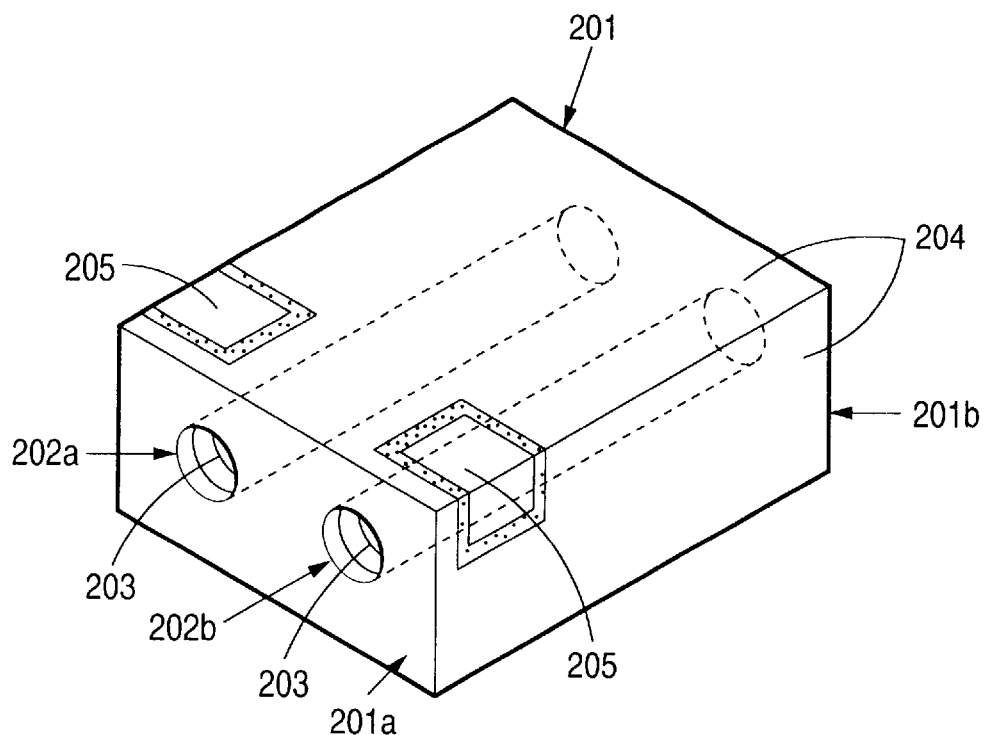
FIG. 3A is a perspective view of a dielectric filter utilizing the dielectric material of the present invention.
Figure 3B:
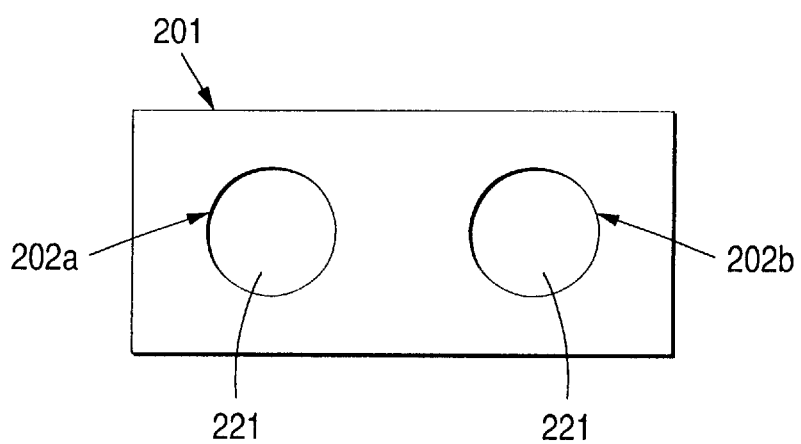
FIG. 3B is a front view taken from the open end surface of FIG. 3A.

For example, the dielectric filter shown in FIGS. 3A and 3B includes resonator holes 202a and 202b.

In the structure shown in FIGS. 3A and 3B, the coupling between the two resonators formed at resonator holes 202a and 202b is inductive coupling, and one attenuation pole is formed in the high frequency range of the pass band. A pair of input/output electrodes 205 are formed at prescribed portions on the outer surface of dielectric block 201, having open end surface 201a and circuited end surface 201b. Inner conductors 203 are formed on the inner surfaces of resonator holes 202a and 202b. The structure also comprises an outer conductor 204, and a step 221.

(4) A Third Example of Dielectric Filter Prepared by Using Dielectric Material of the Invention The dielectric material of the present invention may be used in a dielectric filter such as a microstripline filter.

Figure 4:
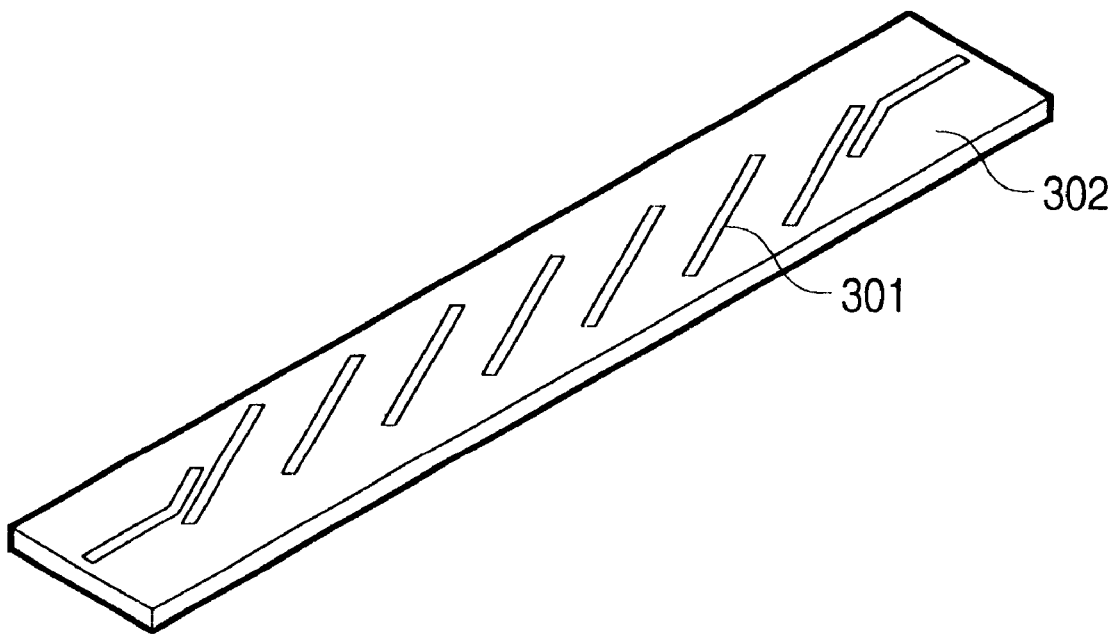
FIG. 4 illustrates a microstripline filter using the dielectric material of the present invention.

FIG. 4 shows an illustration of a single layer circuit board configured as a stripline or transmission line resonator device. In this device, a plurality of microstrip resonance conductors 301 are provide on a dielectric substrate 302 using the dielectric material of the present invention.

According to the present invention, a dielectric material having a relatively large $\in_r$, a small absolute value of $\tau_f$ and a large $Q_u$ and exhibits stable dielectric characteristics can be obtained. Further, these dielectric characteristics can be controlled in conformity with the properties desired for the end use in dielectric parts having small to large sizes by adjusting the amount of the oxygen supplying agent and the kinds and amounts of the rare earth oxides.

What is claimed is:

1. A dielectric material consisting of:

a main ingredient having a composition represented by $xBaO-yRE_2O_3-zTiO_2$, wherein RE represents at least one rare earth element, and x+y+z=100 mol %;

wherein x, y and z in said main ingredient satisfy $0<x\leq27.0$, $0<y\leq30.0$, and $55.0\leq z<100.0$;

at least one alkali metal oxide; and an ingredient derived from an oxygen supplying agent which releases oxygen on heating, wherein the oxygen supplying agent is selected from the group consisting of $MnO_2$, $CuO$, $AgO$, $SnO_2$, $PbO_2$ and a combination thereof.

2. A dielectric material according to claim 1, wherein said oxygen supplying agent is present in an amount of 0.01 to 5.0 parts by weight per 100 parts by weight of said main ingredient.

3. A dielectric material according to claim 1, wherein said RE is at least one of La, Ce, Pr, Nd, and Sm.

4. A dielectric material according to claim 1, wherein said $RE_2O_3$ is represented by composition formula $\{(1-a-b-c-d)Sm.aLa.bCe.cPr.dNd\}_2O_3$, wherein $0\leq a<1$, $0\leq b<1$, $0\leq c<1$, $0\leq d<1$, and $a+b+c+d<1$.

5. A dielectric material according to claim 1, wherein x, y, and z in said main ingredient satisfy $5.0\leq x\leq22.5$, $0<y\leq21.0$, and $62.5\leq z<95.0$.

6. A dielectric filter comprising a dielectric material as claimed in claim 1.

7. A dielectric resonator comprising a dielectric material as claimed in claim 1.

* * * * *